United States Patent [19]

Sinor et al.

[11] Patent Number: 4,963,478

[45] Date of Patent: Oct. 16, 1990

[54] ARTICLE FOR PREFORMING IMMUNOLOGICAL ASSAYS UTILIZING ORGANIC DYES AND METHOD FOR PRODUCING AND UTILIZING SAME

[75] Inventors: Lyle T. Sinor; Ralph A. Eatz; Darryl L. Stone, all of Roswell, Ga.; Fred V. Plapp, Overland Park, Kans.

[73] Assignee: Immucor, Inc., Norcross, Ga.

[21] Appl. No.: 215,041

[22] Filed: Jul. 5, 1988

[51] Int. Cl.$^5$ .................. G01N 33/543; G01N 33/554
[52] U.S. Cl. ...................................... 435/7; 436/518; 436/519; 436/520
[58] Field of Search ............... 436/518, 519, 520, 524, 436/527, 528, 529, 531, 807, 809, 810, 823, 824; 435/174, 176, 177, 805, 7; 427/2

[56] References Cited

U.S. PATENT DOCUMENTS

| | | | |
|---|---|---|---|
| 3,619,371 | 11/1971 | Crook et al. | 424/88 |
| 3,646,346 | 2/1972 | Catt | 436/531 |
| 3,996,344 | 12/1976 | Gross | 436/537 |
| 4,090,919 | 5/1978 | Chibata et al. | 435/99 X |
| 4,360,358 | 11/1982 | Sharma | 435/7 |
| 4,604,348 | 8/1986 | Neurath | 436/809 X |

OTHER PUBLICATIONS

"Depletion by Monolayer Binding of Specific Precursors of Antibody-Forming Cells Directed Against Cellular Antigens", A. D. Nash and W. Boyle, *Immunology*, 1986, 57, pp. 411-417.

"Immunofluorescence with Monoclonal Antibodies on Poly-L-Lysin Coated Slides: an Alternative to Conventional Methods", M. M. Mehta, R. Munker, B. Kranz, E., Thiel and S. Thierfelder, *Blut*, (1983), 47:237-242.

"An Improved Assay for Haemolytic Plaque-Forming Cells", J. C. Kennedy and M. A. Axelrad, *Immunology*, 1971, 20, 253-257.

"A New method for the Irreversible Attachment of Cells or Proteins to Polystyrene Tissue Culture Plates for Use in the Study of Bacterial Adhesion", D. W. McEachran and R. T. Irvin, *Journal of Microbiological Methods*, 5 (1986), 99-111.

"Use of Glutaraldehyde and a Coupling Agent for Proteins and Peptides", Morris Reichlin, *Methods of Enzymology*, 1980; 70; 159-165.

"Erythrocyte Adhesion to Polymer Surfaces", D. R. Absolom W. Zingg, C. Thomson, Z. Policova, C. J. Van Oss, and A. W. Neumann, *Journal of Colloid and Interface Science*, vol. 104, No. 1, Mar. 1985, pp. 51-59.

"Preparing Monolayers of Non-Adherent Mammalian Cells", M. Jules Mattes, Mitsune Tanimoto, Marilyn S. Pollack, and David H. Maurer, *Journal Immunological Methods*, 61 (1983), 145-150.

"Method for Binding Cells to Plastic: Application to Solid Phase Immunoassays for Cell-Surface Antigens", C. H. Heusser, J. W. Stocker, R. H. Gisler, *Methods of Enzymology*, vol. 78, pp. 406-418.

"Preparation of Immobilized Animal Cells", Kjell Nilsson and Klaus Mosbach, *FEBS Letters*, vol. 118, No. 1, Aug. 1980, pp. 145-150.

"Adhesion of Cells to Polystyrene Surfaces", A. S. G. Curtis, J. V. Forrester, C. McInnes, and F. Lawrie, *The Journal of Cell Biology*, vol. 97, Nov. 1983, pp. 1500-1506.

"Entrapment of Enzymes and Microorganisms in Synthetic Cross-Linked Polymers and Their Application in Column Techniques", Klaus Mosback and Rolf Mosbach, *Acta Chemical Scandinavia*, 20 (1966), No. 10. pp. 2807-2810.

"Chemical Activaties of E. Coli Adsorbed on a Resin", Tsutomo Hattori and Choseki Furusaka, *The Journal of Biochemistry*, vol. 48, No. 6, 1960, pp. 831-837.

*Primary Examiner*—Sam Rosen
*Assistant Examiner*—David A. Saunders
*Attorney, Agent, or Firm*—Kokjer, Kircher, Bradley, Wharton, Bowman & Johnson

[57] ABSTRACT

An article for performing solid-phase immunological assays and method for performing assays utilizing the article of the invention. A solid-phase support suitable for immunological assays is stained with an organic dye that has a net-positive charge and a hydrophobic aromatic ring structure. An immunologically reactive component having a net-negative charge is immobilized by the dye to the support through non-covalent interactions. The immunologically reactive component is tightly bound by the organic dye. This is advantageous when performing immunological assays utilizing automated washing instruments. A sample of a biological fluid is added to the article having the immunologically reactive component bound thereto to detect the presence of antigens or antibodies in the biological fluid specific for the bound immunological component. The presence of the antigen-antibody complex may be determined by any known method.

4 Claims, No Drawings

ARTICLE FOR PREFORMING IMMUNOLOGICAL ASSAYS UTILIZING ORGANIC DYES AND METHOD FOR PRODUCING AND UTILIZING SAME

BACKGROUND OF THE INVENTION

This invention relates in general to immunological assays and, more particularly, to an article for use in performing solid-phase immunological assays utilizing organic dyes. The invention further relates to immunological methods for using the article, a method for producing the immunological article and to kits for performing immunological assays that incorporate the article.

In its broadest sense, an immunological assay is a procedure by which an immunologically reactive component attached to a whole cell and present in a biological fluid is detected by measuring its binding with its specific immunological counterpart. The immunologically reactive component can be either an antigen or an antibody and its immunological counterpart would then be the antibody or antigen specific for such component. The immunologically reactive component or its counterpart could additionally be bound to another material or substance that does not destroy its immunological properties.

A wide variety of methods have been developed to detect the presence of the antigen-antibody complex. In a radioimmunological assay, a known amount of a radioactively labeled antigen is added to the fluid in which the unknown antigen is present. This fluid is reacted with another mixture containing antibody specific for the antigen. The labeled and unlabeled antigen react with the antibody in proportion to their relative concentrations in the fluid. Following separation of the antibody-bound antigen from the free antigen, the radioactivity of the antigen-antibody complex is then measured.

In an enzyme-linked immunological reaction, the radioactive label is replaced with an enzyme, such as alkaline phosphatase or peroxidase. The amount of antigen or antibody present in the unknown sample is determined by measuring the amount of enzyme reaction product produced over time. This amount is proportional to the amount of antibody present in the test sample.

In order to obtain immunological assay tests having a higher degree of sensitivity and specificity, solid-phase immunological assay procedures were developed. This allows for the component of the antigen-antibody complex in the biological fluid to be separated from other components in the reaction mixture. In a solid phase immunoassay, one component of the immunological reaction, either antigen or antibody, is immobilized onto the surface of a solid-phase support. A number of methods have been developed for directly immobilizing antigens or antibodies to the solid-phase support. One such method employs a triazinyl linking group to immobilize the antigen or antibody to the solid-phase support; another method uses a hydroxy lower alkyl amine to coat a polymeric solid-phase support with antigens or antibodies; a third method utilizes glutaraldehyde to immobilize the antigen or antibody. While these methods have proven useful for the direct immobilization of antigens or antibodies, they have not shown efficacy in immobilizing whole cells, such as erythrocytes, leukocytes, lymphocytes, platelets or other mammalian cells.

It is well-known that antigens are presented on or can be adsorbed to the surface of these types of cells. It has become useful to determine the presence of these antigens in assays for blood groups and infectious disease agents, especially those directly affecting the cellular components of blood. Immobilizing whole mammalian cells to a solid-phase support enables the technician to obtain greater specificity in the results of this type of immunoassay.

A variety of attempts have been made in the past to immobilize whole cells to solid-phase supports. One method uses a chemical means to covalently bond cells to the solid-phase support. This method has found limited use in immobilizing cells because of the high cost of the coupling agents and the limited number of types of cells that can be immobilized under the necessary coupling conditions without destroying the cell's immunological integrity. The primary chemical use to covalently immobilize whole cells has been glutaraldehyde. This chemical has an aldehyde group on either end of the molecule that cross-links the cells to the support. While this method has shown some efficacy in binding cells to solid-phase supports, it has been found that the glutaraldehyde modifies the cell surface which interferes with the immunological reaction.

The most preferred method for immobilizing whole cells to a solid-phase support uses adsorption rather than covalent bonding to create a layer of cells on the surface of the support. The adsorption of cells onto a support depends upon the composition, charge and age of the cell surface. Additionally, the composition, charge and shape of the support material influences the attachment of cells to the support. A problem inherent with adsorption of cells is that the bond of the cells to the support is relatively weak. This problem is exaggerated due to the onset of automated washing instruments utilized in most hospitals and labs performing these assays. The use of automated washing instruments is preferable, if not necessary, to reduce the risk of contamination of the assay by repeated handling of the support. Additionally, due to the highly infectious nature of some blood-related diseases, the risk to the technician performing the test is reduced by methods involving less direct handling. The automated instruments are also necessary in order to perform large quantities of tests in the fastest time possible to enable physicians or others to make diagnoses and to begin treatment as soon as possible.

Presently, the most widely used adsorption technique utilizes poly L-lysine to immobilize cells to polystyrene supports. The bond between poly-L-lysine and the support is ionic in nature and creates a rather weak bond between the cells and the solid-phase support. This weak bond leads to the reduced utility of poly L-lysine as an adsorption means when automated washing instruments are used. The bond between the poly-L-lysine and the cells is too weak to prevent the cells from becoming dislodged during the washing process. If some of the cells forming the layer on the support are so dislodged, the accuracy of the assay is greatly reduced due to non-specific binding of other antigens or antibodies in the specimen to the support itself or to the coupling agent.

It is therefore a primary object of the present invention to provide an article and a method for performing an immunological assay that is well-suited for use with automated washing instruments.

It is a further object of the invention to provide such a method that utilizes an adsorption method of binding cells to a solid-phase support that maintains the integrity of the cell-surface immunological components in order to provide immunological assays with high specificity.

It is another object of the invention to provide a method for detecting the presence of antigens in a biological fluid that utilizes an adsorption method of binding cells to a solid-phase support at a relatively low cost.

It is yet another object of the invention to provide a method for adsorbing whole mammalian cells to a solid-phase support that binds the cells more tightly to the support than presently known methods.

It is still a further object of the present invention to provide a solid-phase support capable of tightly binding whole cells in a manner that greatly reduces the loss of cells from the monolayer of cells adhered to the support when used with automated washers.

It is an aim of the present invention to provide a solid-phase support for use in immunological assays that embodies all of the above-mentioned objects.

It is another aim of the present invention to provide a kit for performing solid-phase immunological assays that incorporates a solid-phase support embodying the objects of the invention.

SUMMARY OF THE INVENTION

We have discovered that the use of organic dyes having a net-positive charge and having a hydrophobic aromatic ring structure can be used for immobilizing an immunologically reactive component attached to whole cells and present in a biological fluid to a solid phase support and provides an advantageous method and article for performing solid phase immunological assays. The organic dye is first coated to the solid-phase support. When an immunologically reactive component having a net-negative charge, such as mammalian cells, erythrocytes, lymphocytes, leukocytes or platelets, comes into contact with the organic dye, the component becomes immobilized by noncovalent means to the dye. This bond between the immunologically reactive cells and the organic dye is of sufficient strength to resist disruption of the cell monolayer when subjected to washing by most automated washers.

DETAILED DESCRIPTION OF THE INVENTION

Solid-phase immunoassays utilize a wide array of articles as the solid support structure. The support often takes the form of test tubes, beads, sheets of material, Petri dishes, membranes, or microtiter plates. Other types of supports or forms of supports are useful in carrying out the aims and objects of the present invention and are equally applicable.

The solid-phase support can be composed of an organic polymer such as polystyrene, polypropylene, polyvinyl chloride or nylon. Any material that can be stained by an organic dye can be utilized as the support for solid-phase immunoassays besides organic polymers, such as glass.

The most preferred solid-phase support for carrying out immunoassays embodying the present invention are microtiter plates having a plurality of recessed wells. The microtiter plates are preferably made of an organic polymer, and most preferably polystyrene.

The solid-phase support utilized must be handled carefully and kept free of contaminating proteins that could affect the immunoassay.

The dyes useful in this invention are those organic dyes possessing a net-positive charge and that have a hydrophobic aromatic ring structure. Any dye having a net positive charge and such a hydrophobic aromatic ring structure that adheres to a solid-phase support has utility in carrying out the objects of this invention.

Many of the organic dyes useful in preparing a solid-phase article for carrying out an immunoassay can be categorized into various classes. One such particularly useful class of dyes are the azo dyes that have a net positive charge. Azo dyes are characterized by the presence of an azo linkage, -N=N-, bringing two aromatic rings into conjunction. This linkage produces a compound that is usually intensely colored. The aromatic rings are often benzene or naphthalene rings. The azo group, -N=N-, may occur once or more in the compound. Monoazo dyes have the basic structure:

where R is an aromatic ring structure. Examples of monoazo dyes include p-ethoxychrysoidin, having the chemical formula $C_{14}H_{17}N_4OCl$ and the structure:

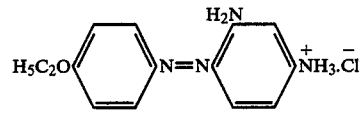

Amidol Black, having the chemical formula $C_{12}H_{10}N_5O_4CL$ and the structure:

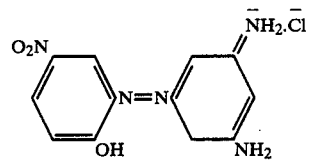

and Alcian Yellow having the chemical formula $C_{38}H_{42}N_8DS_4Cl_2$ and the structure:

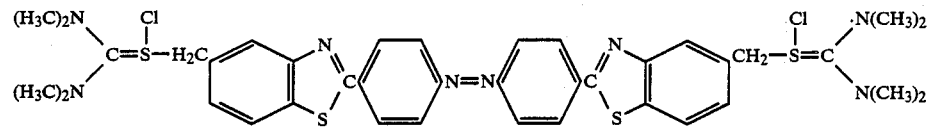

The azo linkage occurs twice in diazo dyes and has the general structure:

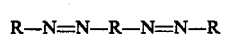

where R is an aromatic ring structure. Examples of diazo dyes useful in this invention include Janus Yellow having the formula $C_{21}H_{21}N_6O_4Cl$ and having the structure:

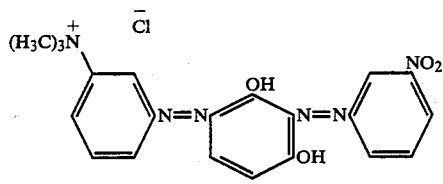

and Janus Red having the formula $C_{26}H_{26}N_5OCl$ and having the structure:

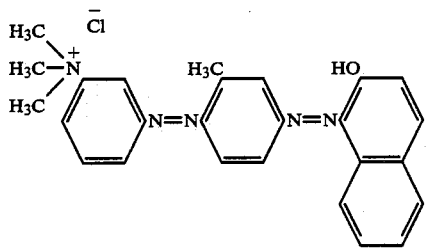

Dyes with greater than two azo linkage groups are known as polyazo dyes. An example of a polyazo dye is Luxol Fast Blue G having the chemical formula $C_{102}H_{97}N_{19}O_{13}S_4$ and having the structure:

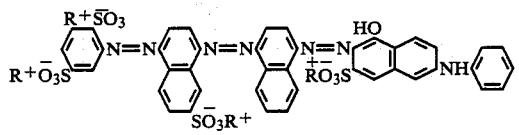

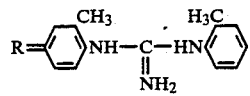

Another class of organic dyes having a net positive charge useful in the present invention are the diazonium and tetrazonium salts. Both include the structure:

R—N≡N where R is an aromatic ring structure. Diazonium salts contain only one of these structures, whereas tetrazonium salts contain two. Examples of diazonium salts include diazobenzene having the chemical formula $C_6H_5N_2Cl$ and having the structure:

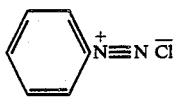

and Fast Scarlet having the chemical formula $C_6H_3Cl_4N_2Zn_{1/2}$ and having the structure:

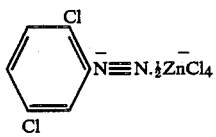

An example of a tetrazonium salt is Fast Blue B which has the chemical formula $C_{14}H_{12}O_2N_4Cl_8Zn$ and has the structure:

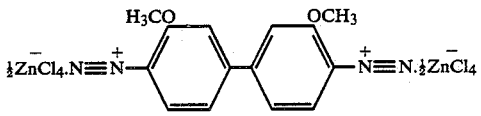

A third class of organic dyes useful in the present invention are the tetrazolium salts. Tetrazolium salts are also known as tetrazoles and have the basic structure:

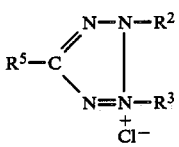

where R is an aromatic ring structure. Examples of a tetrazolium salt are iodonitrotetrazolium having the chemical name 2-(p-iodophenyl)-3-(p-nitrophenyl)-5-phenyl tetrazolium chloride; the chemical formula $C_{19}H_{13}N_5O_2ICl$ and having the structure:

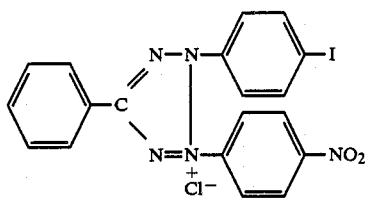

and ditetrazolium chloride having the chemical name 3,3' (4,4'-Di-o-anisylene)-2,2'-di(p nitrophenyl)-bis(5-phenyl), the chemical formula $C_{40}H_{30}N_{10}O_6Cl_2$ and the structure:

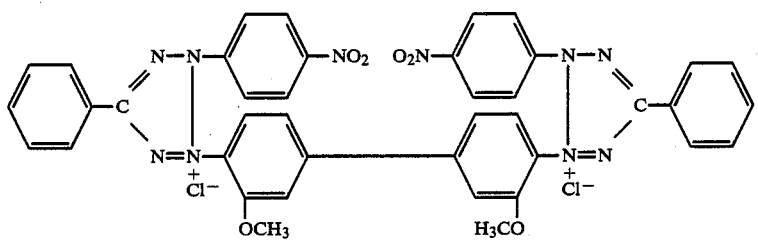

A fourth class of organic dyes for use in the present invention are triphenylmethanes. This class of compounds is characterized by substitution of three (3) of the hydrogen atoms of methane, $CH_4$, with phenyl groups. The general formula is shown as:

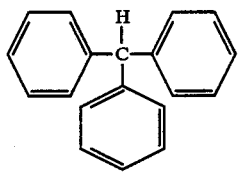

with a specific example of a triphenylmethane being Malachite Green that has the chemical formula $C_{23}H_{25}N_2Cl$ and the structure:

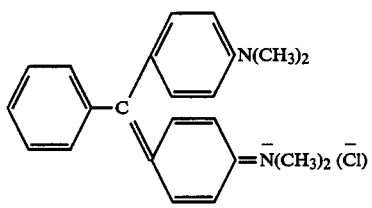

A class of organic dyes categorized under the name xanthenes or acridines, comprises a fifth class useful in the instant invention. Compounds in this class are derivatives of xanthene which has the structure:

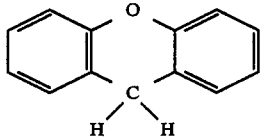

Examples of specific xanthenes or acridines include Acridine Red 3B having the chemical formula $C_{13}H_{10}N_2OCl$ and having the structure:

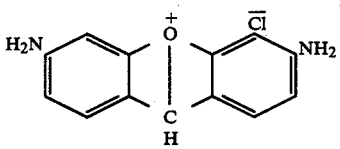

and Atabrine which has the chemical formula $C_{23}H_{32}N_3OCl_3 \cdot 2H_2O$ and has the structure:

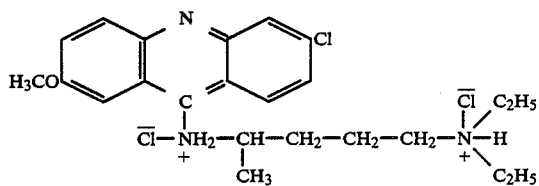

A sixth class of organic dyes can be labeled quinoline dyes. An example of a quinoline dye is pinacyanol which has the chemical formula $C_{25}H_{25}N_2I$ and the chemical structure:

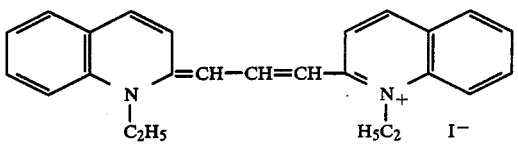

Another class of organic dyes useful in the present invention are called thiazoles. Thiazoles are characterized by the presence of the structure:

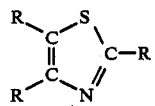

where R is an aromatic ring structure. A specific example of a thiazole is thiaflavine TCN which has the chemical formula $C_{15}H_{19}N_2SCl$ and the chemical structure:

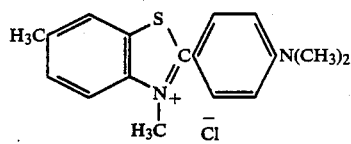

A further group of organic dyes having utility in the subject invention includes classes of dyes called indamines, azins, aminoazins, safranins and thiazins. The indamine dyes are compounds embodying the basic structure:

R—N=R where R is an aromatic ring structure. Phenylene Blue is a specific example of an indamine and has the chemical formula $C_{12}H_{12}N_3Cl$ and the chemical structure:

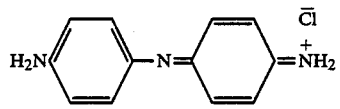

The dyes of the azin group are derivatives of phenazin which has two forms of its chemical structure:

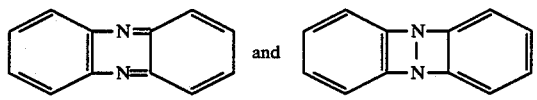

If one or more amino groups are introduced into a phenazin, an aminoazin is formed. Neutral Red is an example of an aminoazin and has the chemical formula $C_{15}H_{17}N_4Cl$ and the structure:

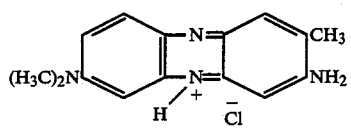

Safranins are dyes similar to azins but where one of the nitrogen atoms of the azin group is pentavalent and has a benzene ring attached to it. A specific example is phenosafranin which has the chemical formula $C_{18}H_{15}N_4Cl$ and the structure:

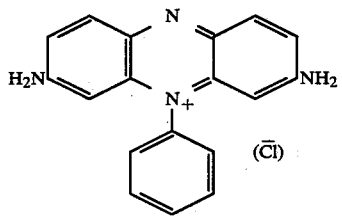

Thiazins are characterized by the substitution of a sulfur atom in place of one of the nitrogen atoms of an azin group. Specific examples of thiazins include Azure C having the chemical formula $C_{13}H_{11}N_3SCl$ and the structure:

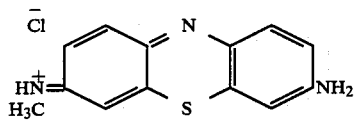

and Methylene blue having the chemical formula $C_{16}H_{18}N_3SCl$ and the structure:

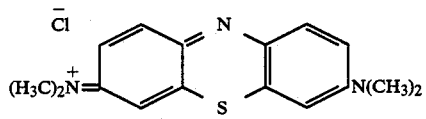

A final exemplary class of organic dyes useful in this invention are the phthalocyanins. These are cyclic compounds having isoindole groups surrounding a central metal atom, typically copper, where the linkage bridge atoms are —N= structures. Specific examples of phthalocyanins include Alcian blue having a structure:

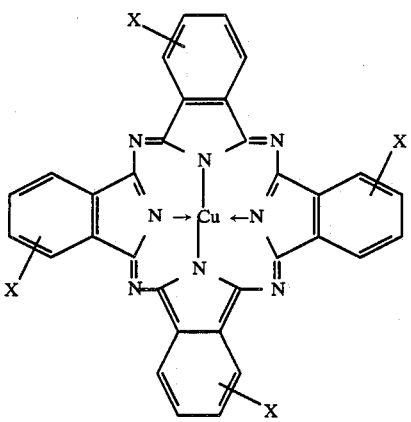

where X is an onium group:

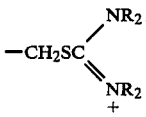

and quinolinic phthalocyanin having a structure:

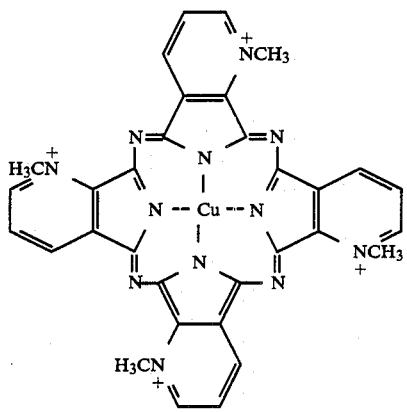

The above classes and examples of dyes are to be considered illustrative and not in a limiting sense. Any organic dye having a net-positive charge and a hydrophobic aromatic ring structure capable of staining a solid-phase support is considered to be within the scope of this invention.

Any of these dyes can be independently produced by known methods or can be obtained commercially through known sources.

The component that is immobilized by the organic dye can be any immunologically reactive component that has a net-negative charge and can undergo hydrophobic bonding while attached to a whole cell The whole cells that can be used may be from human or animal sources. Erythrocytes, platelets, leukocytes and lymphocytes and mammalian cells are especially suited for use in immunological assays of the present invention. Particularly useful are erythrocytes and platelets from human sources.

Once an appropriate dye and support material is chosen, the dye is coated onto the support. To do this, a liquid solution of the dye is prepared and an excess amount of the dye solution is contacted with the support for a period of time sufficient for the dye to coat and stain the support. The dye may be dissolved in any suitable liquid, such as isotonic saline or a suitable alcohol if necessary. The dye binds to the support by noncovalent interactions such as ionic, hydrogen, van der Vaal's and hydrophobic bonding. The dye can be incubated with the support for extended periods of time or the support can be dipped in a solution containing the dye and washed immediately depending upon the staining capacity of the dye.

Two dyes in particular have been used in preparing solid-phase supports for use in immunoassays pursuant to the present invention; Alcian Blue and Alcian Yellow. To prepare a solid phase support using Alcian Blue, the dye is first dissolved in isotonic saline to obtain a concentration of between 1 ug/ml-1 g/ml of the dye in the saline. A sufficient quantity of the dye solution, 25-350 microliters per well in a microtiter plate, is then applied onto the organic polymer support and left in contact with the support for a period of time sufficient for the dye to bind to and stain the support. Excess dye is rinsed from the support.

The use of Alcian Yellow is slightly different in that Alcian Yellow is not soluble in aqueous solutions. Therefore, a quantity of Alcian Yellow is first dissolved in a sufficient quantity of 100% methanol and then an equal volume of isotonic saline is added to the mixture. The useful concentration range is again between 1 ug/ml-1 g/ml, and 25-350 microliters is a sufficient quantity to be applied to wells of a microtiter plate.

As is inherently understood, any of the organic dyes useful for this invention may be prepared and used in similar fashion. Individual procedures to dissolve individual dyes into solution may be necessary and are encompassed within the scope of this invention, such procedures being known to those skilled in the art.

The immunologically reactive component must next be immobilized onto the dye coated solid-phase support. This is accomplished by placing a quantity of a solution containing the component onto the dye coated support and allowing the component to settle onto the support either by gravity or by centrifugation and allowed to contact with the dye for a sufficient period of time to adhere thereto. Unbound immunological reactive components can then be washed away with a saline solution. This leaves a layer of the immunologically reactive component immobilized to the dye coated support.

In a preferred embodiment of the present invention, whole cells, especially erythrocytes or platelets, are the immunologically reactive component to be immobilized onto the dye coated support. These whole cells have a net-negative charge and adhere by noncovalent or hydrophobic interactions to organic dyes which have a net-positive charge and a hydrophobic aromatic ring structure. These noncovalent interactions include ionic, hydrogen, van der Vaal's and hydrophobic bonding. Contacting cells with the organic dye creates a monolayer of cells over the surface of the support which is extremely useful in preforming immunoassays as it eliminates some non-specific binding potential. To create a cell monolayer, the cells to be immobilized must first be washed free of contaminating proteins in the biological fluid. If this is not done, these proteins will, by adsorption, become immobilized to the dye and block the dyes positive charge. This would prevent the cell from adsorbing to the dye. The cells may be washed in a suitable liquid such as tissue culture fluid, water, isotonic saline or phosphate buffered saline, having a pH range between 5-10.

The washed cells are then suspended in either isotonic saline or PBS and permitted to come into contact with the dye either by gravity or centrifugation. After a period of time sufficient to allow interaction of the cells with the dye to achieve adherence thereto, unbound cells are washed away with saline which leaves a monolayer of cells immobilized to the dye coated solid-phase support. The solid-phase support is now ready for use in performing immunoassays for the detection of antigens or antibodies, if present, in a biological test fluid. Any method of detection used in immunochemistry for detecting the presence of the antigen-antibody complex may then be employed to quantify the assay, such as solid-phase red cell adherence, immunofluorescence, radioimmunoassay, or ELISA (enzymelinked immunosorbent assays).

In an alterate embodiment, the immobilized cell monolayers may be used to adsorb antibodies specific for the antigens upon the cell surface. In this situation, the immobilized antibodies can then be used to detect antigens on the surface of other cells or in a biological specimen, followed by traditional assay procedures.

A solid phase support prepared in accordance with the instant invention also has particular utility in the detection of antibodies to erythrocytes, platelets or lymphocytes. Many antibodies of clinical importance are found in patient or donor sera. Some antibodies may cause decreased red cell survival as the result of hemolytic transfusion reactions, hemolytic disease of newborns or autoimmune hemolytic anemia. Other antibodies can cause immune destruction of platelets. In vitro antibody detection tests reveal the presence of these antibodies in patient or donor sera.

In an assay to detect IgG antibodies to erythrocytes, platelets, or lymphocytes, a solid-phase support, typically a U-bottomed microtiter plate, treated with an organic dye having a net-positive charge is utilized. A quantity of previously washed and prepared erythrocytes, platelets or lymphocytes, is added to each dye coated well. The cells are centrifuged onto the surface of the microplate wells where they ionically, non-covalently, bond to the dye coated well and become immobilized thereto. Excess, unbound cells are washed away by hand or by instrument. A quantity of patient or donor serum or plasma is added to the cell coated well and allowed to incubate for a sufficient period of time. If antibodies specific for the cells are present in the patient specimen, they bind immunologically to the monolayer of cells. Nonspecific or unbound antibodies and other components in the specimens are washed away.

To detect the presence of antibodies bound to the cells, indicator red blood cells are added to the microplate wells and centrifuged. Indicator red blood cells are erythrocytes that have been coated with anti-immunoglobulin molecules. If the patient specimen contained antibodies specific for the cell monolayer, the anti-immunoglobulin on the indicator cells will adhere to the antibody (immunoglobulin) that is bound to the cell monolayer causing adherence of the indicator cell to the monolayer; this is a positive reaction. If no antibodies in the patient specimen were specific for the cell monolayer, the anti-immunoglobulin indicator cells will pellet into a discrete and discernible button in the bottom of the well after centrifugations; this is a negative reaction.

The invention also encompasses kits for performing solid-phase red cell adherence immunoassays for the determination of immunoglobulins (antibodies) in patient or donor sera. In particular, the immunoassay kits are to detect the presence of antibodies specific for erythrocytes, platelets or lymphocytes. The kit comprises a microtiter plate having a plurality of U-bottomed recessed wells. The microplate has been treated with an organic dye having a net positive charge according to the teachings of the invention. In a preferred embodiment, the dye used is Alcian yellow. The microtiter plate is supplied in a sealed, foil or plastic pouch, to which a dessicant has been added. The kit further contains a vial of a low ionic strength solution containing glycine, FD&C violet #1 dye and a preservative, preferably sodium azide at 0.1%; a suspension of indicator red cells coated with an anti-human immunoglobulin and suspended in a buffered solution with preservatives, preferably chloramphenicol at 0.25mg/ml and neomycin sulfate at 0.1mg/ml, in a sealed vial; and vials containing known antibodies to the cells being treated, either erythrocytes, lymphocytes or platelets, in at least two different concentrations to use as positive controls as well as a vial containing no antibodies to use as a negative control. The kits may provide vials containing the cells to be coated to the microtiter plate for use in forming the monolayer of cells for the assay. A book or pamphlet of instructions will also be provided.

The following examples are given by way of illustration only and have no limiting character.

EXAMPLE 1

To perform an immunoassay for the detection of antibodies specific for antigens on the surface of erythrocytes, a microtiter plate having a plurality of U-bottomed recessed wells is washed in phosphate buffered saline (PBS) and air dried. A solution of Alcian Blue is prepared by dissolving the dye in isotonic saline to a concentration of 100mg/ml. 250 microliters of the dye solution is added to the wells and incubated for 15 minutes. Excess dye is then washed away using an automated washer such as the Bio-Tek Model EL 402. A solution of suspended erythrocytes is washed in PBS to remove contaminating proteins. A quantity of the cell suspension is added to each well and the microplate is centrifuged in a Sorval GLC-2B with a rotor capable of accommodating the microplate. Centrifugation is performed at 190xg for 5 minutes. Excess or unbound cells are removed by washing 4-6 times with isotonic saline through standard use of the automated washer. Next, a quantity of the test specimen is added to the wells in varying dilutions. The specimen is allowed to incubate in the wells for up to 15 minutes at 37° C. Excess test sample is removed and the plate washed 4-6 times in isotonic saline. Each well is then assayed for the presence of antibodies bound to antigens on the surface of the cells by any standard immunoassay technique such as ELISA.

EXAMPLE 2

The teachings of the present invention can be utilized in assays to determine the blood type group of human red blood cells. A microtiter plate is prepared as in Example 1. A quantity of human group A red blood cells is added to some of the dye coated wells and allowed to adhere and become immobilized thereto by centrifugation. Excess cells are washed away be an automated washing instrument. The cell monolayers are sensitized with anti-A immunoglobulin and washed to remove excess immunoglobulin. Another set of wells are prepared in a similar manner with human group B cells sensitized with anti-B immunoglobulins.

A sample of red blood cells of unknown type are added to the wells and centrifuged for 1 minute. If the sample cells are group A cells, they will adhere to the anti-A immunoglobulin on the cell monolayer, showing a positive reaction for group A blood type. Group A cells will not adhere to the anti-B immunoglobulin on the group B cell monolayer and a negative reaction is shown by a discrete button in the bottom of the microplate well following centrifugation.

EXAMPLE 3

A kit incorporating the teachings of the present invention can be prepared for the detection of unexpected IgG antibodies to erythrocytes. A microtiter plate having a plurality of recessed U-bottomed wells is coated with the organic dye Alcian yellow. Approximately 35-50 microliters of a washed and suspended red blood cell solution is added to a group of wells in the plate. The plate is centrifuged for 5 minutes at 190xg. Excess unbound cells are removed and the plate washed 4-6 times with isotonic saline. The washes are performed by standard use of an automated washing instrument. This reduces the risk of contamination of the plate and to the technician performing the assay. 70-100 microliters of a low ionic strength solution is added to each well. 35-50 microliters of either a known standard or a sample of the patient or donor sera or plasma is then added to each well. The plate is incubated at 37° C. for at least 15 minutes. The mixture is decanted from the plate and again washed 4-6 times with isotonic saline as above. 35-50 microliters of indicator red blood cells previously sensitized with rabbit anti-human IgG is added to the wells. The plate is immediately centrifuged at about 450xg for 1 minute. The plate is placed on an illuminated surface and examined for adherence or absence of adherence to the red cell monolayer. A positive reaction is seen by adherence of the indicator cells over the reaction surface. A negative reaction forms a discrete button of indicator red cells at the bottom of the wells showing no adherence.

EXAMPLE 4

To perform an immunoassay for the detection of antibodies specific for antigens on the surface of human astrocytoma cells grown in tissue culture, a solution of alcian blue is prepared by dissolving the dye in an isotonic saline solution at a concentration of 1 mg/ml. 300 microliters of the dye solution is added to U-bottom microtiter plate wells and incubated for up to 30 minutes. Excess dye is washed away using an automated microplate washer. A solution of suspended astrocytoma cells in tissue culture fluid is washed in PBS to remove contaminating proteins. A quantity of the cell suspension is added to each alcian blue coated well and the microplate is centrifuged in a Sorval GLC-2B with a rotor capable of accommodating the microplate. Centrifugation is performed at 190 xg for 5 minutes. Unbound cells are removed by washing PBS using an automated microplate washer. Next, a quantity of test specimen believed to contain human antibodies specific for astrocytoma antigens, is added to the wells. The specimen is allowed to incubate in the wells for 30 minutes at 37° C. Excess test sample is removed and the plate is washed 4-6 times with PBS, 35-50 microliters of indicator red blood cells previously sensitized with rabbit anti-human immunoglobulin is added to the wells. The plate is immediately centrifuged at 450 xg for 1 minute. The plate is examined for adherence or lack of adherence to the astrocytoma cell monolayer. A positive reaction is seen by adherence of the indicator cells over the reaction surface. A negative reaction forms a discrete button of indicator red cells at the bottom of the wells showing no adherence.

Having thus described the invention, what is claimed is:

1. A method for performing a solid-phase immunoassay for the purpose of determining the presence of an immunologically reactive component in a biological fluid by detecting its adherence to its immunological counterpart which is attached to whole cells, said cells being free of contaminating proteins, comprising the steps of:

providing a solid-phase support coated with an organic dye and selected from the group consisting of azo dyes, diazonium salts, tetrazonium salts, tetrazolium salts, triphenylmethanes, xanthenes, acridines, quinolines, thiazoles, indamines, azins, aminoazins, thiazins and phthalocyanins coated thereon;

placing a quantity of said whole cells on said coated support;

immobilizing said whole cells to said organic dye in a manner presenting said whole cells above said organic dye;

contacting said biological fluid to said support for a sufficient period of time to allow said immunologically reactive components in said fluid to bind to said immunological counterpart;

removing any excess fluid from said support; and assaying for the presence of said immunologically reactive component bound to said immunological counterpart.

2. The method as set forth in claim 1, wherein said cells are selected from the group consisting of erythocytes, lymphocytes, leukocytes, platelets and tissue cells.

3. The method as set forth in claim 1 wherein said immunologically reactive component is an antibody present in serum or plasma and said whole cells are mammalian cells, erythrocytes, lymphocytes, leukocytes, or platelets.

4. The method as set forth in claim 1 wherein said assaying for the presence of said immunologically reactive component is determined by the addition of indicator red blood cells.

* * * * *